United States Patent [19]

Menzel et al.

[11] Patent Number: 4,756,831

[45] Date of Patent: Jul. 12, 1988

[54] PROCESS AND APPARATUS FOR REMOVAL OF NITRATE FROM SURFACE AND GROUND WATER, IN PARTICULAR DRINKING WATER

[75] Inventors: Roman Menzel; Peter Hoffmann, both of Lingen; Klaus-Dieter Vorlop, Braunschweig, all of Fed. Rep. of Germany

[73] Assignee: Noell GmbH

[21] Appl. No.: 869,101

[22] Filed: May 30, 1986

[30] Foreign Application Priority Data

Jun. 5, 1985 [DE] Fed. Rep. of Germany ....... 3520160

[51] Int. Cl.⁴ ............................ C02F 3/30; C02F 3/34
[52] U.S. Cl. ..................................... 210/617; 210/605;
210/611; 210/93; 210/150; 210/202; 210/247;
210/257.1; 210/261; 210/903; 435/182
[58] Field of Search .................. 210/616–618,
210/150, 151, 903, 605, 202, 611, 93, 257.1, 261,
247; 435/175, 177, 182, 180

[56] References Cited

U.S. PATENT DOCUMENTS 4,469,599 9/1984 Gros et al. ........................ 210/617
4,576,718 3/1986 Reischl et al. ..................... 210/617

FOREIGN PATENT DOCUMENTS 0046901 3/1982 European Pat. Off. ........... 210/617
3,312,579 10/1984 Fed. Rep. of Germany ...... 210/605
2337576 9/1977 France .............................. 210/903

OTHER PUBLICATIONS

Hollo et al.; "Denitrification and Removal of Heavy Metals from Waste Water by Immmobilized Microorganisms"; found in (Mar. 1979).

Primary Examiner—Benoit Castel
Attorney, Agent, or Firm—Toren, McGeady & Associates

[57] ABSTRACT

Process for recovering nitrate from surface and ground water, in particular drinking water, by means of biological denitrification, in which the nitrates contained in the water are reduced to gaseous nitrogen in a reactor by means of a biocatalyst having immobilized cells trapped in a gel or polymer. The "micrococcus denitrificans" that is preferably used requires for its metabolism added hydrogen and carbon that is present in the water in the form of dissolved carbon dioxide. Using a biocatalyst of immobilized cells and of the bacterial strain used, expensive after-purification is unnecessary because of increased bacterial count in the pure water outlet, and no undesirable by-products are formed.

13 Claims, 1 Drawing Sheet

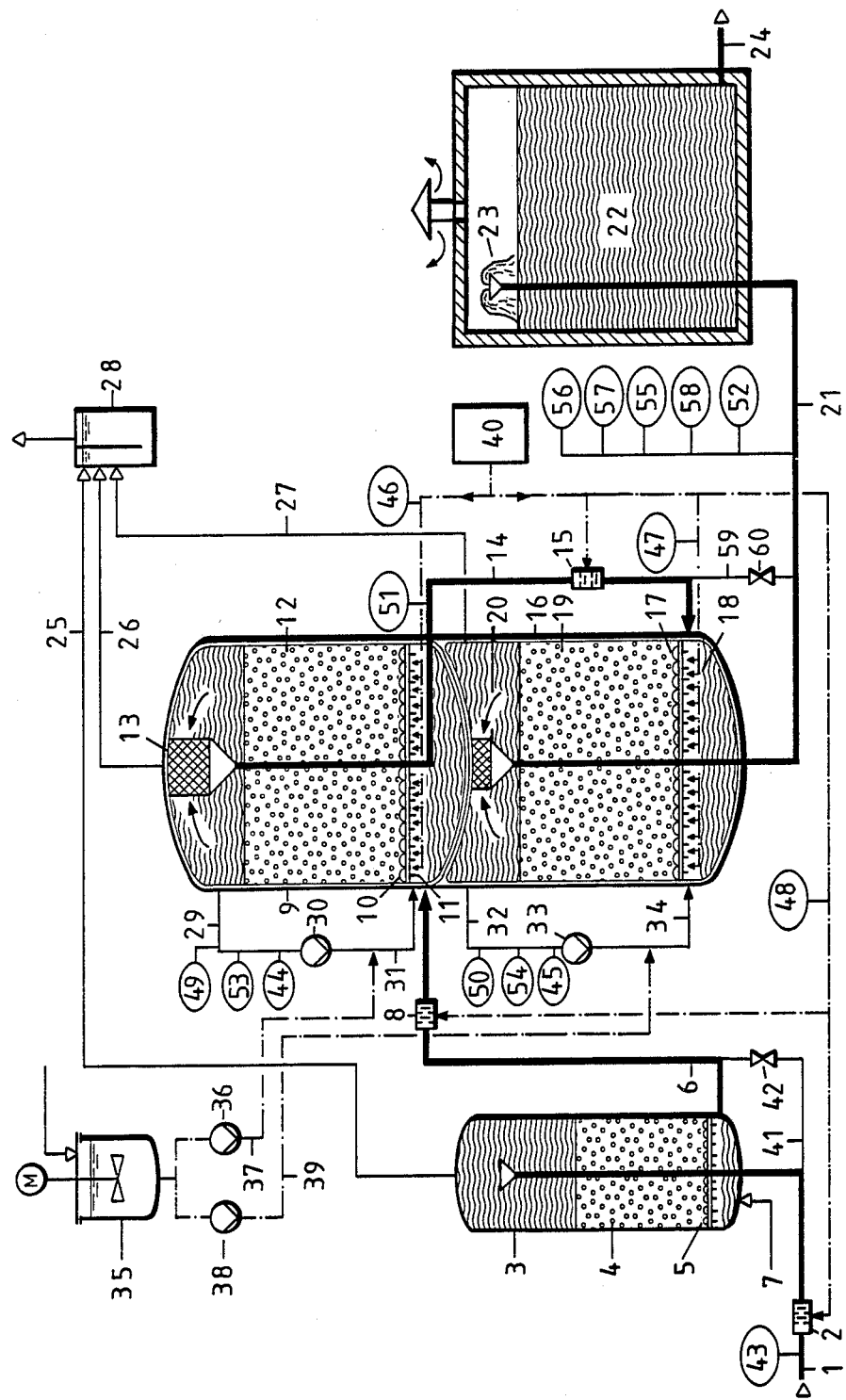

PROCESS AND APPARATUS FOR REMOVAL OF NITRATE FROM SURFACE AND GROUND WATER, IN PARTICULAR DRINKING WATER

FIELD OF THE INVENTION

The invention relates to a process and apparatus for removing nitrate from surface and ground water, in particular from drinking water, by means of biological denitrification.

BACKGROUND OF THE INVENTION AND PRIOR ART

In many water supply sources a great increase in the nitrate content above 50 mg/l $NO_3^-$/l has been recorded, caused inter alia by over-employment of fertiliser to agricultural land and inappropriate disposal of animal sewage. After the connection between high nitrate values, and e.g., cancer of the digestive organs became known, new standards were worked out for 1985 by the European Community, which for nitrates permit an index of 25 mg/l $NO_3^-$/l and a highest permissible concentration of less than 50 mg/l $NO_3^-$/l in drinking water. Hence in many cases treatment cannot be avoided to ensure lower nitrate concentrations in drinking water.

In the article "Removal of nitrate from drinking water by means of biological denitrification" by Ch. Frank and W. Dott, Bonn, published in Biotech.—Forum—internationale Zeitschift für Biotechnologie, ¾, 84, pages 53–57, investigations of such biological processes are described. In these processes bacteria were fixed on the most varied carriers, such as surface growth (adsorption) with nutrient material, percolating filters, immersion bodies, pumice, active carbon, expanded polystyrene balls, foam, (aerated plastics) etc., and used in appropriate reactors in water and waste water treatments.

Two different biological processes should be distinguished:

Lithotrophic (also known as autotrophic) denitrification, in which the addition of hydrogen or elemental sulphur as an electron donor is necessary. Here the dissolved carbon dioxide present in water serves as the source of carbon.

Organotrophic (also known as heterotrophic) denitrification, in which the addition of a carbon carrier such as, e.g., methyl or ethyl alcohol, sugar, molasses, acetic acid, methane etc. is necessary.

In the biological process hitherto used in practice dosing with methanol or ethanol is preferred owing to the shorter reaction time. With this approach, under certain operating conditions (e.g. overdosing or too short a reaction time) undesired by-products such as, for example, formaldehyde and acetaldehyde can be formed, which are classified according to the MAK (maximum work-place concentration) -value guidelines as substances which may be carcinogenic. Hence these processes require expensive control and monitoring systems, which present additional treatment requirements and expenditures.

If instead other carbon carriers such as, for example, sugar, molasses or acetic acid are added, then although according to the present state of knowledge no suspicious reaction products are formed, nevertheless because of long reaction times such processes require larger reaction volumes, which mean a substantial expenditure on plant and investment.

Furthermore all known systems for the denitrifying bacteria used for biological denitrification consist of carriers with surface growth (adsorption), and are therefore susceptible to toxic matter such as, for example, metal ions (chromium, iron, copper, etc.) and require an additional pretreatment step.

Finally the dosing of the water with a source of carbon required in the process necessarily leads to an increase in the bacteria present in the water. Hence such processes are to be judged not only by the reduction of the nitrate loading. The changed bacteriological situation in the purified water delivered and the absolutely necessary after-treatment by, for example a multilayer filter plant, must also be taken into consideration. Here, besides the quantitative effect of the bacterial count, the question of the kinds present comes to the fore. Thus it has been found that after the denitrification reactor, bacterial counts of the order of $10^4$ to $10^5$/ml are present in the water, which can only be reduced by after-treatment, e.g. filtration with intermediate aeration, to the order of $10^2$ to $10^3$/ml usual in treated water.

PROBLEM OF THE INVENTION

The problem underlying the invention is to provide a process and a device of the kind mentioned above that require short reaction times and small expenditure on apparatus and lead to no undesirable by-products and no increase in the count and kinds of bacteria in the purified water.

SUMMARY OF THE INVENTION

This problem is solved by the use of a new kind of biocatalyst with chosen immobilised DENI-cells which—contrary to other carrier systems with surface growth (adsorption) on a solid-state body—are cross-linked in a gel or polymer structure (core) and also firmly entrapped in a cellfree and for cells impermeable protective polymer layer.

Such a biocatalyst is described in German patent application No. P 34 32 923.4, which is not a prior publication, with reference to the production of antibiotics or ethanol, waste water treatment or for the production of sparkling wine. This reference is hereby incorporated by reference in the present application.

As described in German patent application No. P 34 32 923.4, a biocatalyst is obtained by surrounding a cell-containing core with a cell-free protective layer of a cross-linked gel which is impermeable to the cells. The biocatalyst is surrounded with an additonal layer of a cross-linked gel which is prepared so that it does not contain cells to ensure that the surface of the biocatalyst is safely free of active cells. The gels used for immobilizing may be gels which cross-link due to temperature reduction, or gels which require the addition of a special cross-linking agent.

The core containing the cells may be prepared in a conventional manner, i.e., it may have cells already immobilized in a gel. The core is formed preferably by introducing the gel-forming liquid containing the cells into a cross-linking agent, so that beads or pearls or the like are formed. By utilizing the cross-linking agents still contained in the core, the beads are now preferably dipped into the same gel-forming liquid as it has been used for the core. As a result of the cross-linking agent diffusing out of the core, a thin protective layer is formed on the core. The thickness of the protective layer can be controlled by the concentration of the gel-forming liquid and the reaction time. After the protective layer has been formed, the biocatalyst is again dipped into the cross-linking agent, so that the protective layer is cross-linked in a stable manner.

Instead of the two-stage process described above, a single-stage process can also be used. In that case, the core containing the cells is surrounded with the gel-forming liquid which forms the protective layer prior to cross-linking. The core may remain liquid. The cells are introduced into the gel-forming liquid without being mixed therewith. This can be achieved by adjusting different viscosities of the core liquid and of the gel-forming liquid. Subsequently, the entire arrangement may be dipped into a cross-linking bath which may contain a cross-linking agent or may merely ensure a rapid temperature drop in order to cross-link the gel.

It is also possible to provide for the core a gel-forming liquid containing the cells and to surround the liquid with an appropriate gel-forming, cell-free liquid and to dip it immediately into a cross-linking bath. The cross-linking agent penetrates the protective layer so quickly that the immobilization of the cells in the core takes place in time to prevent that cells penetrate into the protective layer.

The cell-free protective layer composed of the gel forms very fine pores through which the cells cannot penetrate, while the cross-linking agent or a nutrient liquid can penetrate.

The biocatalyst can be prepared with the known cross-linking gels. As a thermally cross-linking gel, Agar may be used. As gels which cross-link with a cross-linking agent may be used, for example, the ionically cross-linking gels Ca-alginate, K and/or Ca-kappa-carrageenan, chitosan, Mg- or Ca-pectinate, carboxy-methyl cellulose, or the covalently cross-linking gels polyacrylamide, polyurethane, polyepoxide, silica gels or the like.

The separation of the biocatalysts shall now be explained in more detail with the aid of the following examples.

EXAMPLE 1

A catalyst in the form of beads is obtained by preparing a 3.2% Na-alginate solution by stirring 3.3 g Na-alginate into 100 ml distilled water and subsequently autoclaving the solution for 15 minutes at 1 bar excess pressure and 121° C. Yeast cells (saccharomyces bayanus; Lalvin C1108 Boehringer KG) are suspended in a 0.9% NaCl solution. The 3.3% Na-alginate solution is now mixed into the suspension. The suspension is then dropped into a precipitation bath composed of a 2% $CaCl_2$ solution. When the drops reach the precipitation bath, a gel bead having a size of about 3 mm is created because the exchange of $Na^+$ ions with $Ca^{2+}$ ions results in the cross-linking of the alginate to the gel. The beads obtained by the ionotropic gel formation are for further cross-linking agitated for 30 minutes in the $CaCl_2$ solution. Subsequently, the beads are screened off and washed with tap water for several times. The beads are then rinsed with distilled water in a 0.5 or 0.2 Na-alginate solution. The alginate solution is obtained in the same manner as described above. The diffusion of Ca ions from the gel beads into the Na-alginate solution results in the formation of a sheath of Ca-alginate round the beads. After 5 minutes of agitation, the thickness of the sheath is sufficient, so that the Na-alignate solution can be poured off. The beads are washed with tap water and are rinsed in a 2% $CaCl_2$ solution. After a cross-linking time of one hour, the beads are washed with tap water for several times.

EXAMPLE 2

A 3.3% Na-alginate solution is prepared as in Example 1. A second 1% Na-alginate solution is prepared in the same manner. Both solutions are autoclaved for 15 minutes under the conditions described with respect to Example 1. The dry yeast mentioned in Example 1 is suspended in a 0.9% NaCl solution and introduced into the 3.3% Na-alginate solution. The alginate cell suspension is adjusted in such a way that 1 g dry yeast is contained in 10 g Na-alginate solution. The biocatalyst is prepared by boiling a cotton thread in order to remove unwanted flavor. The cotton thread has a length of about 18 cm with knots every 1.5 cm. The thread is subsequently washed in tap water and used as a carrier for the catalyst gel. The cotton thread is dipped into the alginate cell suspension until the thread is well impregnated. The knots in the thread have the purpose to facilitate adherence of the alginate gel. For the ionotropic gel formation, the cotton thread is now introduced with the alginate cell suspension adhering thereto into a 2% $CaCl_2$ solution. The catalyst thread is left for 30 minutes in the $CaCl_2$ solution which is slightly agitated. Subsequently, the thread is washed with tap water and dipped into the 1% Na-alginate solution. By diffusion of gel ions from the gel on the thread into the Na-alginate solution, a sheath of Ca-alginate is formed around the catalyst thread. For further cross-linking of the alginate sheath, the catalyst thread is placed for one hour into a 2% $CaCl_2$ solution which is slightly agitated. Subsequently, the catalyst thread is washed with tap water for several times and is irradiated for 5 minutes with a 6 Watt ultraviolet lamp.

EXAMPLE 3

A 3.3% Na-alginate solution is prepared as in Example 1. a 1% aqueous Na-kappa-carrageenan solution is prepared in the same manner. Both solutions are autoclaved for 15 minutes under the conditions described with respect to Example 1. The dry yeast mentioned in Example 1 is suspended in a 0.9% NaCl solution and is placed in the 3.3% Na-alginate solution. The alginate cell suspension is adjusted in such a way that 1 g dry yeast is in 10 g Na-alginate solution. The biocatalyst is prepared by using a polyethylene cork as a carrier. A flat rod with holes is attached to the cork. The rod is dipped into the alginate cell suspension until it is covered with a film of this suspension. The rod is then placed in a 2% $NaCl_2$ solution for the ionotropic gel formation and is left for 30 minutes in this $CaCl_2$ solution. Subsequently, the rod is washed and dipped into the 1% Na-carrageenan solution. By diffusion of Ca ions from the gel on the rod into the Na-carrageenan solution, a sheath of Ca-carrageenan is formed. For further cross-linking of the carrageenan sheath, the rod is placed for one hour in a slightly agitated solution consisting of 10 g KCl+10 g $CaCl_2$/1 l water. The catalyst is subsequently washed and irradiated for 5 minutes with a 6 Watt ultraviolet lamp.

The biocatalysts obtained in accordance with the above examples can be dried and stored in a suitable form.

By the use of such a biocatalyst according to the invention there results an increased concentration of biomass in the reactor bed, whereby decomposition of nitrate is achieved in the shortest time. Compared with carrier systems and an open-pore structure the improvements that can be achieved in respect of reaction time and of the expenditure on apparatus are more than 60%.

After fairly long use the biocatalyst can, if necessary, be exchanged without difficulty. This is further facilitated by the fact that the biocatalyst can be stored in dried form and is immediately ready for use, and that no difficulties arise in setting up short-term self production in-situ. Since the inactive biocatalyst is in every respect harmless, no special chemical treatment is needed before disposal by discharge into the drains or sewage-treatment plant.

The short-term occurrence of toxic impurities in the water to be denitrified, such as, for example, metal ions, in concentrations not appreciably higher than that of the calcium in the natural water, has no negative effects.

Further, the establishment of different bacterial cultures and an increase in the bacterial count, such as can occur in carrier systems with surface growth (adsorption), is excluded. For this reason no costly after-treatment, e.g. by multilayer filtration to return the bacterial count in the purified water discharge to the prescribed values, is necessary.

Preferably the strain "micrococcus denitrificans" is used for the denitrification. This is an autotrophic strain that requires hydrogen for its metabolism. The growth rate can be controlled by appropriate dosing with hydrogen. The carbon requirments are met by the strain from the carbon dioxide dissolved in the water, and only nitrate decomposition occurs. The formation of undesirable reaction by-products such as, for example, aldehydes, can thus not occur in the treated water, If necessary the biological denitrification can be performed in two stages in order to meet the prescribed nitrate contents in the pure water discharge.

Insofar as the nitrate-bearing natural water exhibits increased oxygen concentrations, significant savings can be made in the volume of the reaction vessel for the biological denitrification if in a preliminary step a catalytic deoxidation of the water is performed by oxidation of added hydrogen.

For optimisation of the process it is necessary to adjust the pH-value of the water in the biological denitrification to an optimum value. This is advantageously done by dosing with acid, e.g. hydrochloric acid.

The apparatus according to the invention for carrying out the process consists, in its simplest form, of a reaction vessel comprising a biocatalyst bed, a water supply pipe and a water discharge pipe and a hydrogen dosing pipe with a recirculation circuit between the discharge and water inlet to the biocatalyst bed to control the rate of denitrification.

A pH-adjusting and measuring device, preferably having an acid dosing pump, can be connected to this recirculation circuit.

Depending on the nitrate concentration in the natural water on the one hand and the permitted residual nitrate content in the purified water, two or more reaction vessels, connected in series, can be provided.

The reaction of the oxygen in the natural water takes place in a reaction vessel connected before the biological denitrification and having a catalyst bed, a hydrogen dosing line and water inlet and outlet lines.

To adapt the plant in a simple manner to differing nitrate-loaded natural water having different degrees of oxygen concentrations, bypass lines with valves therein are provided to bridge the biological denitrification reaction vessel or vessels and/or the catalytic deoxidation reaction vessel.

BRIEF DESCRIPTION OF THE DRAWING

In the drawing;
The FIGURE is a a diagrammatic representation of an apparatus according to the invention.

DESCRIPTION OF A PREFERRED
EMBODIMENT OF THE INVENTION

The invention will now be described in more detail with reference to an example shown diagrammatically in the drawing.

The natural water to be treated passes into a reaction vessel 3 via a supply line 1 and a static mixer 2 through which hydrogen is measured in from a hydrogen dosing device 40. In this reaction vessel 3 is arranged a precious metal containing catalyst bed 4 resting on a support base 5. Palladium or other precious metals are for example used as the catalyst. The reaction vessel 3 is made in the form of a closed pressure vessel designed for a working pressure of at least 3 bar. The water supplied emerges from the inlet pipe 1 above the catalyst bed 4 in the reaction vessel 3, flows downwards through the catalyst bed 4 and is removed via a discharge pipe 6. The catalyst bed 4 can be back-washed in known manner for periodic loosening up via a special water connection 7 through the support base 5. With negligble concentration of oxygen in the natural water the overall water stream can, by closing valve 42 in the by-pass pipe 41, be led to outlet pipe 6 without passing through reaction tank 3.

The discharge line 6 leads via a further static mixer 8 for hydrogen into a reaction vessel 9 that forms the first stage of the biological denitrification. In the lower part of the reaction vessel 9 a supporting base 10 is provided for a biocatalyst bed 12 through which the natural water to be denitrified is led. At the upper end of the reaction vessel 9 the partially denitrified water enters, via a filter device 13, a discharge line 14 through which it passes into a reaction vessel 16 that forms the second stage of the biological denitrification. The reaction vessel 16 is of similar construction to the reaction vessel 9 and has a supporting base 17 with a biocatalyst bed 19 arranged thereon. The water to be denitrified passes through this reaction vessel 16 also from the bottom to the top, and leaves the reaction vessel 16 via a filter device 20 and a discharge line 21. In principle there is also the possibility (not shown in the diagram) of leading the stream of water from the upper chamber of the reaction vessel 9 or 16 into its lower part, by suitable arrangement of the inlet line 11 and the discharge lines 14 and 21 on the reaction vessel 9 and 16. The discharge line 21 leads into a collecting vessel for purified water 22 in which a splash overflow (cascade) 23 is provided for enrichment of the denitrified water with oxygen.

To control the degree of denitrification each of the two denitrifying stages is provided with its own controllable circulating system. The circulating system of the reaction vessel 9 consists of a pipe 29 downstream or upstream of the biocatalyst bed 12, a recirculating pump 30 and a pipe 31 opening below the supporting base 10. The circulating system of the reaction vessel 16 identically consists of a pipe 32, a recirculating pump 33 and a pipe 34. In each of the pipes 29, 32 are arranged a pH-meter 49, 50, a hydrogen content meter 53, 54 and a flow-meter 44, 45.

The pH-meters 49, 50 serves to adjust the pH value in the reaction vessels 9 and 16. This is done by means of metering pumps 36, 38 connected to the pipes 31, 34 by pipes 37, 39. By means of the metering pumps 36, 38 and e.g. hydrochloric acid, is withdrawn from a container 35 and fed in the desired quantity into the reaction vessels 9, 16. An additional monitoring of the pH value of the purified water takes place in the pipe 21 by means of a pH meter 52.

The hydrogen content meters 53, 54 serve to control the supply of hydrogen to the mixers 2, 8 and 15 via a hydrogen metering device 40.

If desired the hydrogen can be introduced directly into the reaction vessel 9 via a distributing system 11 and into the reaction vessel 16 via a distributing system 18. In the supply line 1, the lines 29, 32 and the lines leading from the hydrogen metering device 40 are arranged additional flow-meters 43 to 48 by means of which the throughput through these lines is measured.

A by-pass line 59 with a valve 60 is provided between the discharge line 14 from the reaction vessel 9 and the discharge line 21 from the reaction vessel 16 so that a larger or smaller proportion of the water flowing from the first reaction vessel can be led directly to the pure water collection vessel 22 without flowing through the reaction vessel 16. The amount of water flowing through the by-pass line 59 depends on the nitrate loading of the natural water and the permissible residual nitrate content in the purified water.

This residual nitrate content in the purified water is determined by means of a measuring device 56 for the $NO_3$ content, a measuring device 57 for the $NO_x$ content, and a measuring device 58 for the $NO_2$ content. In addition yet another hydrogen content meter 55 is provided at this position.

Gas lines 25, 26, 27 through which the reaction vessels 3, 9, 16 can be vented lead from the reaction vessels 3, 9, 16 to the exterior via a water seal 28.

What is claimed is:

1. A process for removing nitrates from surface and ground water and from drinking water by biological denitrification comprising reducing said nitrates to gaseous nitrogen by contacting said water with a biocatalyst comprising a core of immobilized denitrifying organism cells trapped and cross-linked in an ionophoric gel or polymer and surrounded by an additional cell-free protective layer, said layer being impermeable to cells and consisting of a gel or polymer.

2. A process according to claim 1 further including a step of catalytic deoxidation of the water by oxidation with added hydrogen in the presence of a precious metals catalyst performed before the biological denitrification.

3. A process according to claim 1, wherein the strain "micrococcus denitrificans" is present in the biocatalyst.

4. A process according to claim 1, wherein the biological denitrification is performed in two or more stages.

5. A process according to claim 1, wherein the pH of the water in the biological denitrification is adjusted to 7 by the addition of acid.

6. Apparatus for removing nitrates from natural waters comprising, in combination:
means for supplying water to be denitrified;
a source of hydrogen;
a first static mixer for oxidizing said water and including means for receiving said water from said means and hydrogen from said source;
a first reactor receiving said water from said first static mixer and containing a bed of precious metal catalyst;
hydrogen supply means connected operatively to said first reactor;
a catalytic bed in said reactor having an upper section receiving said water;
an outlet for said water communicating with said first reactor;
a second static mixer including means for receiving water from said reactor and means for receiving hydrogen from said hydrogen supply means;
a second reactor vessel constituting the first stage of denitrification;
conduit means connecting said second mixer to said second reactor;
said second reactor containing a biocatalyst bed consisting of immobilized cells trapped in an ionophoric gel of polymer and surrounded by an additional cell-free protective polymeric layer;
a third reactor forming the second denitrification stage of said apparatus and fluidly communicating with and surmounted by said second reactor;
said third reactor also containing a biocatalyst bed and a discharge line wherein connected with said third reactor are a recirculating pump, a pH meter, a first hydrogen meter and a flow meter;
means for measuring the residual nitrate content of water discharging from said third reactor;
and a collecting vessel communicating therewith.

7. Apparatus according to claim 6, having by-pass lines and associated values bypassing said biological denitrification reactors and/or the first reactor.

8. Apparatus according to claim 6 said means for measuring residual nitrate content comprising measuring devices for $NO_3$ $NO_x$ and $NO_2$ contents.

9. The apparatus of claim 6, having conduit means for introducing hydrogen directly into said second and third reactors.

10. The apparatus of claim 6, having by-pass means for flowing water directly from said second reactor to said collecting vessel without flowing through said third reactor.

11. The apparatus of claim 10, further including a second hydrogen meter between the third reactor and the collecting vessel.

12. The apparatus of claim 10, further including a water seal and gas lines connecting said reactors to said collecting vessel;
a source of supply of oxygen supplying oxygen to said collecting vessel;
controllable circulating systems for controlling the degree of denitrification of each of said denitrification stages;
said systems consisting each of a conduit connecting the upper part of said second and third reactors thereto to vent gases from the apparatus.

13. The apparatus of claim 6, wherein the collecting vessel includes a splash overflow of enriching the water issuing from said third reactor with oxygen.

* * * * *